United States Patent [19]

Kloos

[11] Patent Number: 5,038,261
[45] Date of Patent: Aug. 6, 1991

[54] OPERATING LAMP WITH ADJUSTABLE MOUNTING

[75] Inventor: Thomas Kloos, Offenbach am Main, Fed. Rep. of Germany

[73] Assignee: W. C. Heraeus GmbH, Hanau am Main, Fed. Rep. of Germany

[21] Appl. No.: 594,356

[22] Filed: Oct. 9, 1990

[30] Foreign Application Priority Data

Oct. 7, 1989 [DE] Fed. Rep. of Germany ....... 3933596

[51] Int. Cl.$^5$ ............................................. F21V 21/00
[52] U.S. Cl. .................................. 362/286; 362/386; 362/804
[58] Field of Search ............... 362/233, 271, 272, 286, 362/386, 419, 428, 804; 315/149, 152

[56] References Cited

U.S. PATENT DOCUMENTS

| | | | |
|---|---|---|---|
| 4,517,632 | 5/1985 | Roos | 362/389 |
| 4,578,575 | 3/1986 | Roos | 362/804 X |
| 4,639,838 | 1/1987 | Kato et al. | 362/804 X |
| 4,884,008 | 11/1989 | Bossier et al. | 315/152 |

FOREIGN PATENT DOCUMENTS 3227494  2/1984  Fed. Rep. of Germany .

Primary Examiner—Stephen F. Husar
Attorney, Agent, or Firm—Frishauf, Holtz, Goodman & Woodward

[57] ABSTRACT

An operating-room light fixture features a cardanic mounting connected to an overhead beam or other stationary support by joints or linkages which rotate about horizontal and vertical axes. After setting of the optimal illumination zone into the operating plane, that zone's coordinates, and the associated coordinates of the lamp housing, are stored as values in a computer. Upon intentional or unintentional spatial displacement of the lamp housing, angle sensors in the joints, and a distance sensor in the lamp housing, furnish data to the computer, which calculates a compensating adjustment and carries it out by applying control signals to positioning motors in the cardanic mounting, until the axis or axes of the light beam(s) again place the optimal illumination zone on the operating field.

8 Claims, 3 Drawing Sheets

OPERATING LAMP WITH ADJUSTABLE MOUNTING

Cross-reference to related patents and pending application, the disclosures of which are hereby incorporated by reference:

U.S. Ser. No. 07/292,515, LUGER, Des. for Operating Room Light Fixture; U.S. Pat. No. 4,884,008, corresponding to German DE-OS 37 23 009, BOSSLER et al./W. C. HERAEUS GmbH;

U.S. Pat. No. 4,517,632, corresp. to German DE-OS 32 43 709, ROOS; German Application DE-OS 32 27 494, MENKE, published Feb. 2, 1984.

FIELD OF THE INVENTION

The present invention relates generally to a method of manipulating an operating room lamp having at least one light beam extending from the bottom of its lamp housing, and, more particularly, to a system in which the movement of the fixture is carried out using a cardanic adjustable mounting. The lamp axis is aligned with the operating field as an illumination zone by at least one adjusting element. The adjusting element is controlled with automatic feedback using a distance meter responsive to acoustic or electromagnetic signals. The invention includes the operating lamp itself.

BACKGROUND OF THE INVENTION

U.S. Pat. No. 4,884,008 and corresponding German DE-OS 3723009 disclose an operating theater lamp with multiple light beams projecting from the bottom on the lamp housing. These beams are aligned in such a way that they overlap in the operating field and form an intensified illumination field. The alignment is done with the aid of an ultrasonic distance meter located in the fixture. The meter generates a signal representing the distance between fixture and operating field, and this signal is fed to a control circuit as a command or guidance value. In the control circuit, this guidance value is compared with the angle setting of the light beam which serves as the control value. In the event of deviation or difference between these two values, an adjusting signal is applied until the control value agrees with the guidance value. The associated electrical circuit inhibits the control circuit from reacting to passage, through the light beam, of suddenly appearing measurement targets, e.g. the hands or head of the surgeon. The release of the beam adjustment mechanism therefore occurs either by manual actuation of a handle located on the lamp housing or by sensed increase in distance, such as occurs upon deepening of the operating incision. In this way, one can achieve an automatic, trouble-free beaming or direction of the light, without special equipment.

Further, MENKE DE-OS 32 27 494 discloses an operating lamp, for dental and oral surgery procedures, in which the light beam is kept automatically aligned on the mouth area of the patient throughout adjustments to the dental chair or couch. See discussion at U.S. Pat. No. 4,884,008, col. 2, lines 10-30. The associated tracking mechanism uses an ultrasound transmitter 32 located on or near the patient's head, ultrasound receivers 38 spatially separated around the treatment room, and a direction finding circuit 40. The tracking is done using servo- or stepper-motors by which the holding of the lamp in specified positions or inclinations can be carried out. Due to the need to locate an ultrasound transmitter in the immediate vicinity of the operating field to be illuminated, such an operating lamp is unusable in general surgery. In particular, one would have to expect errors in adjustment, as well as difficulties in handling and sterilization.

SUMMARY OF THE INVENTION

Accordingly, it is an object of the present invention, upon intentional or unintentional displacement of the operating lamp, to readjust the beam direction setting so that the originally set illumination zone (operating incision) will again be exactly illuminated without new displacement of the lamp fixture. The optimal adjustment of the light beam or beams should be carried out automatically.

Briefly, the spatial coordinates/alignment of the initial lamp position and the spatial coordinates of the initial illumination zone are determined and stored. When any relative movement occurs, a compensating adjustment to the lamp position and/or orientation is calculated and carried out. The storage of the initial positions is triggered manually, with the initial lamp position and lamp pointing direction determined by angle measurements at all joints, and the initial coordinates of the illumination zone determined by distance measurement along the beam or fixture axis. After movement of the lamp, its position and the orientation of its lighting axis are determined by new angle measurements. The differences between the previously stored coordinate values and the newly measured coordinate values are processed in a control circuit to generate adjustment signals to the positioning motors connected with the joints of the cardanic mounting, and, by means of these motors, the lamp housing is displaced until the lighting axis intersects with the originally set illumination zone.

In an operating lamp with only a single light beam, the profile or side-section of the light beam is optimally adjusted along the housing axis in dependence upon the distance between lamp housing and illumination zone (operating field) by focussing, and this is stored as a digital value.

In an operating lamp with multiple light beams, which are aligned with the operating field using at least one adjusting element, the beams overlapping to form an intensely illuminated zone, one first makes adjustments to place this zone on the operating field. Then the coordinates of this zone, and the coordinates of the lamp housing, are determined by angle measurements at the joints or linkages, and by distance measurement between the intensely illuminated zone and the lamp housing, and these coordinates are stored as digital values. In the event of displacement, the light beams are so readjusted, in dependence upon the distance between lamp housing and illumination zone, that the beams again overlap to form an intensely illuminated zone.

The values furnished by the angle meters and the distance meter are translated by coordinate transformation into Cartesian spatial coordinates. The differences between the original coordinate values and the measured post-displacement coordinate values on the X-, Y-, and Z-axes are used to generate adjustment signals for the positioning motors. The spatial coordinates of the illumination field (operating field) serve as the Command or desired value. The servo-mechanisms adjust until the Actual value coincides with the Command value.

In the apparatus according to the invention, for carrying out the method, at least both linkages of the cardanic adjustable mounting are provided with adjusting motors, and all linkages of the mounting are provided with a meters or transducers. Angle meters and distance meter Sept. 20, 1990 are connected to the input of an electronic computer or microprocessor which store the values furnished by the angle meters and distance meter Sept. 20, 1990. The computer has at least two outputs connected respectively to an adjusting motor for adjustment of the cardanic mounting of the lamp housing. The setting of the optimal illumination zone is accomplished using a handle connected to the lamp housing. The handle can be removed for sterilization. The handle features a button which is pressed, when the optimal setting has been achieved, to store the coordinate values.

It is of course also possible to provide a handle which automatically stores the coordinate values whenever the operator or attendant releases the handle. The lamp fixture is then provided with sidegrips for moving it.

Since the elements of the mounting, i.e. the rods or framing connected to the joints, have unvarying dimensions, it is possible to specify or convey the position and alignment of the lamp housing merely by measurements of the angles at the joints. The distance between lamp and the operating field is furnished by distance measurement performed acoustically or electromagnetically. See, for example, the ultrasonic distance sensor 5 discussed in U.S. Pat. No. 4,884,008, BOSSLER et al., column 7. The measured angle values and distance value to the operating field are subjected to coordinate transformation, so that the spatial coordinates of the lamp housing and the operating field can be calculated and stored. The deviations in the coordinate system, measured after displacement of the lamp, serve as adjustment signals for the positioning motors located in the cardanic mounting of the lamp housing.

An advantageous feature of the present invention is that the angle sensors, positioning motors, computer, and actuating element can be integrated or retro-fitted into conventional operating room light fixtures, so that one can dispense with construction of additional apparatus or housings.

A further feature is that the angle sensors operate throughout a complete 360° range, so that an unambiguous association with the position and alignment of the lamp housing is always possible. The distance measurement also provides a double-check o the coordinate values furnished.

DRAWINGS

FIG. 3 is a side view of an alternate embodiment having multiple (four) light sources.

The angles labeled with the Greek letter Phi are defined with reference to the associated joints and the associated coordinate axes. For greater legibility, the angles are illustrated only partially.

DETAILED DESCRIPTION

Figure 1:
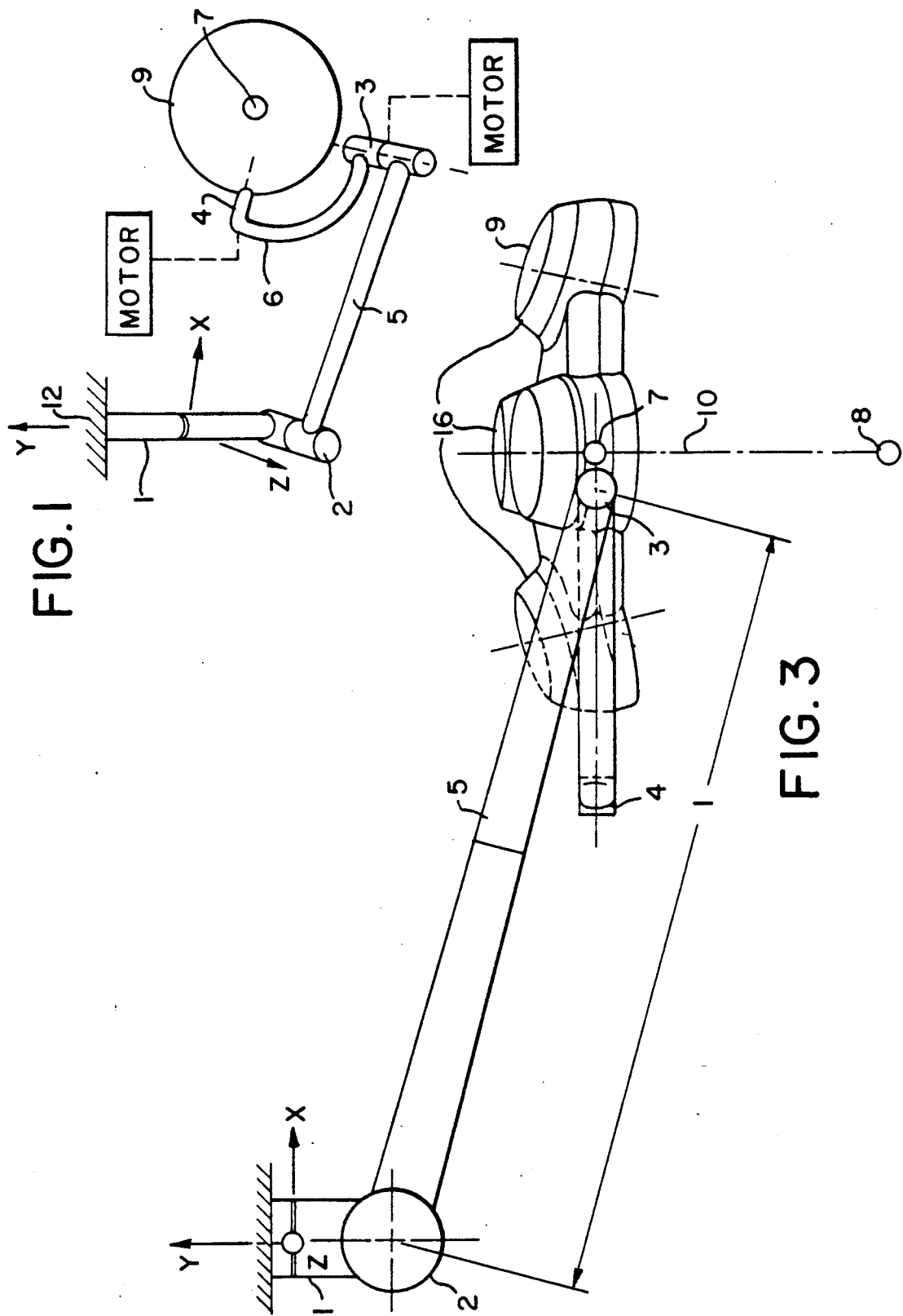
FIG. 1 is a perspective view of the mounting of the invention, together with a lamp housing, indicated schematically.

FIG. 1 illustrates a ceiling, overhead beam, or other stationary support 12, to which is fastened a pivot 1 whose lower part is rotatable 360° about a vertical axis Y. The lower part of pivot 1 is connected to a tilt joint 2 which is rotatable about a horizontal axis Z through a range of about 180°. Joint 2 is connected by a rod 5 to a pivot joint 3, which is rotatable through a 360° range, about a horizontal axis. Joint 3 is connected to a bowed rod 6, preferably quarter-circular, having at its other end a further pivot joint 4 whose axis of rotation is perpendicular to that of pivot joint 3. Pivot joint 4 connects to the actual lamp housing 9 of the operating room lamp.

Pivot joints 3 and 4 form the cardanic mounting of the operating lamp and define the rotation axes for the lamp housing. These axes of rotation intersect at reference point 7 as shown, which is preferably central to the lamp reflector(s).

Angle sensors in each of joints 1, 2, 3, 4 measure respective angles $Phi_1$, $Phi_2$, $Phi_3$, and $Phi_4$ and furnish those values to a computer for coordinate determination. The angle sensors in joints 1, 2, 3, and 4 are preferably optically sampled or scanned coded drums which generate a digital signal corresponding to the rotation angle of the joint. For ease of illustration, the angle sensors and the positioning motors in joints 3 and 4, needed for displacement of the lamp housing, have been omitted from the drawings. In the positioning motors, the part to be moved is connected to the motor rotor, that is, in joint 3 the rotor of the positioning motor is connected to bowed rod 6, and in joint 4 the rotor is connected to lamp housing 9. It is, of course, also possible to carry out the rotations using gears instead.

Figure 2:
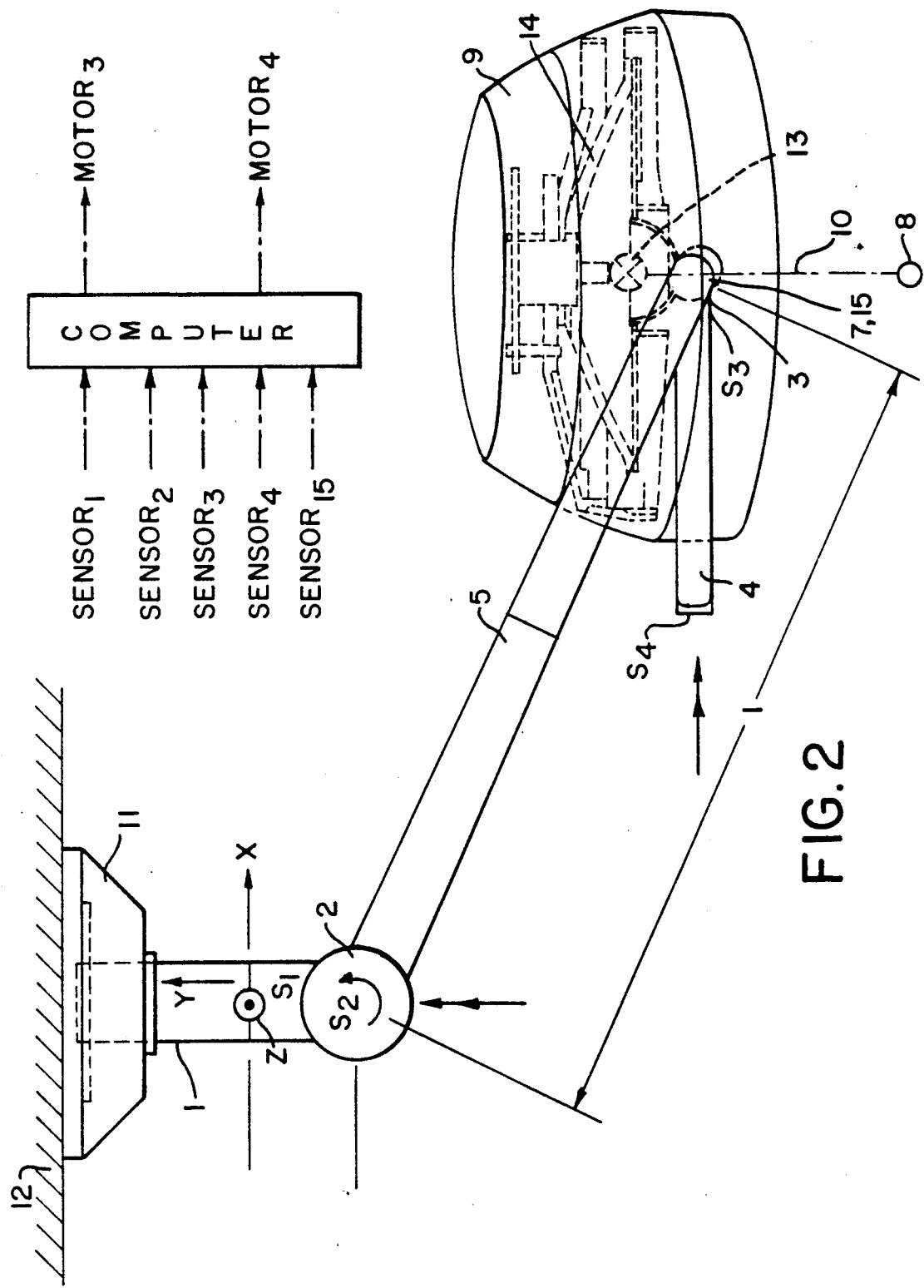
FIG. 2 illustrates an embodiment of the operating lamp having a single light source, with the lamp housing in cross-section.

FIG. 2 illustrates pivot 1 fastened to ceiling 12 using a pad or bracket 11. The designation of the joints corresponds to that in the FIG. 1 embodiment. The sectioned lamp housing 9 features a single light source 13, whose emitted light is directed in the direction of illumination axis 10 with the aid of a reflector arrangement 14 (cold light reflector). Focussing is possible by altering the spacing between light source 13 and reflector 14. At or near reference point 7 is an ultrasound sensor 15 for determining the distance between illumination zone 8 (operating plane) and reference point 7 of the lamp housing 9.

FIG. 3 illustrates an operating lamp with a multi-beam lamp housing consisting of individual emitters 16 which are arranged in a ring configuration on a carrier. The light coming out of emitters 16 is beamed, with the aid of the ultrasound sensor, to form an intensely illuminated zone in the operating plane 8. The ultrasound sensor generates a distance-dependent signal which is fed to a servo or control circuit which so aligns the light beams of the individual emitters, using adjusting elements, that the intensely illuminated zone is maintained in spite of any distance fluctuations.

The position of the joints is determined, with reference to FIG. 3, as follows: the origin of the Cartesian coordinate system is located in joint 1, with the axis X extending horizontally and the axis Y running along the rotation axis of pivot joint 1. Axis Z is normal to axes X and Y and thus extends upward out of the plane of the drawing. The position of joint 3 is thus dependent upon the length of rods 5 and the rotations in joints 1 and 2, designated as angles $Phi_1$ and $Phi_2$. The length of rods 5 is defined Sept. 20, 1990 to be l:

$$x_3 = 1 \cdot \cos\phi_2 \cdot \cos\phi_1$$

$$y_3 = 1 \cdot \sin\phi_2$$

$$z_3 = 1 \cdot \cos\phi_2 \cdot \sin\phi_1$$

For the coordinates of point 7, the following relations apply, the distance of the rotation axis of joint 2 at the zero point being defined as $y_2$, and the distance between joint 3 and point 7 being defined as m:

$$x_7 = o + 1 \cdot \cos\phi_2 \cdot \cos\phi_1 + o$$

$$y_7 = y_2 + 1 \cdot \sin\phi_2$$

$$z_7 = o + 1 \cdot \cos\phi_2 \cdot \sin\phi_1 +$$

Figure 4:
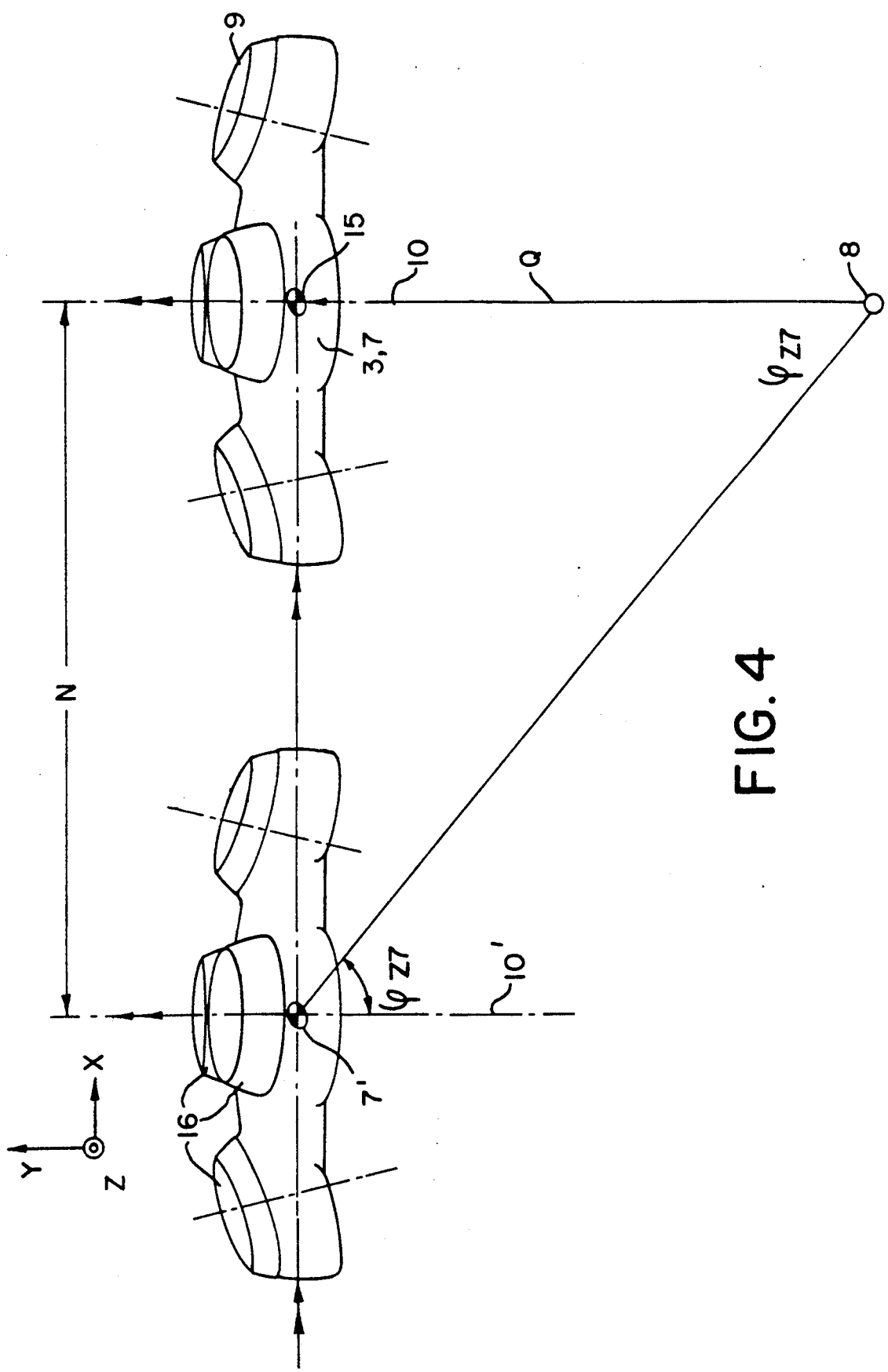
FIG. 4 is a schematic before-and-after view of the lamp of FIG. 3, showing the angular relationships in the X-Y-Z frame when the lamp housing is spatially displaced.

According to FIG. 4, the following relationships apply for the angle setting of the axes normal to the lamp bodies with reference to the coordinate system:

$$\phi z_7 = \phi_2 - \phi_3$$

$$\phi x_7 = \phi_4$$

Point 8, symbolizing the operating plane, is determined by distance measurement. In the simplest case, the lamp, as shown in FIG. 4 rests with its central point 7 over operating point 8.

The spacing between central point 7 and operating plane 8 is designated as Q. So, for displacement of lamp housing 9 by a distance N from position 7 to position 7′, the following relations apply:

$$N_x = x_7 - x_{7'}$$

$$N_y = y_7 - y_{7'}$$

$$N_z = z_7 - z_{7'}$$

According to FIG. 4, the following relations are true for the new angular setting:

$$\phi z_{7'} = \arctan \frac{Q - N_y}{N_x}$$

$$\phi x_{7'} = \arctan \frac{Q - N_y}{N_z}$$

The thus-derived angles are then adjusted by the positioning motors by rotations at joints 3 and 4. The resetting of the intensely illuminated zone by overlapping of the light beams is accomplished, as previously explained, by automatic feedback control using the distance meter.

Various changes and modifications are possible within the scope of the inventive concept. In particular, one could enhance the adjustability of the operating lamp of the present invention by installing further joints, also equipped with respective angle sensors. The angle sensors could be Hall generators instead of optical sensors.

I claim:

1. A method of automatically aligning an operating room lamp, said lamp having
   a lamp housing (9) emitting at least one light beam Sept. 20, 1990
   a cardanic mounting (1,2,3,4,5,6) supporting said housing and including a joint (2) Sept. 20, 1990 rotatable about a horizontal axis and at least one further joint (1) Sept. 20, 1990 rotatable about a vertical axis;
   at least one means for positioning an axis of said light beam onto an operating field to produce an illuminated zone, said means including a respective positioning motor at each of said joints (3,4);
   a distance sensor mounted on said housing (9) for sensing distance between said housing and said operating field, and connected to said positioning means for automatic feedback control,
   an angle sensor at each joint (1,2,3,4) of said cardanic mounting; and
   a computer, connected to outputs of said sensors and to control inputs of said motors;
   comprising the steps of
   reading distance and angle data from said sensor into said computer;
   calculating, based on said data, coordinates of said lamp housing and of said operating field;
   storing said coordinates in said computer;
   monitoring said distance and angle sensors and thereby detecting relative displacement between said lamp housing and said operating field;
   testing any detected displacement to determine whether such displacement exceeds predetermined limits; and, if so,
   applying control signals to at least one of said motors until a predetermined relationship between said lamp housing and said operating field is restored.

2. A method according to claim 1, further comprising adjusting alignment of a light beam axis (10) as a function of distance between said lamp housing (9) and said operating field (8).

3. A method according to claim 1, further comprising aligning axes of a plurality of light beams so that said light beams overlap to form an intensely illuminated zone.

4. A method according to claim 1, wherein said calculating step comprises
   translating said distance and angle data into Cartesian coordinates and, in the event of undesired deviation from previous coordinates, applying control signals to said positioning motors as a function of differences between previous coordinates and current coordinates of said lamp housing (9).

5. Operating room lamp having
   a lamp housing (9) emitting at least one light beam Sept. 20, 1990;
   a cardanic mounting (1,2,3,4,5,6) supporting said housing and including a joint (2) Sept. 20, 1990 rotatable about a horizontal axis and at least one further joint (1) Sept. 20, 1990 rotatable about a vertical axis;
   at least one means for positioning an axis of said light beam onto an operating field to produce an illuminated zone; and
   a distance sensor connected to said positioning means for automatic feedback control,
   wherein, in accordance with the invention,
   said positioning means includes a respective positioning motor at each of said joints (3,4);
   each joint (1,2,3,4) of said cardanic mounting is equipped with an angle sensor;
   said distance sensor (15) is mounted on said housing (9) for sensing distance between said housing and said operating field;

a computer is provided, connected to outputs of said sensors and to control inputs of said motors, said computer processing output signals from said sensors to determine coordinates of said lamp housing and of said operating field, and generating control signals to said motors to automatically adjust lamp housing position and alignment with respect to said operating field.

6. Operating room lamp according to claim 5, wherein at least two light beams are emitted by respective light sources (16) in the lamp housing (9), and means are provided for aligning optical axes of said beams with an operating field (8) so that said beams overlap to form a intensely illuminated zone in said operating field.

7. Operating room lamp according to claim 5, wherein each angle sensor optically scans a coded surface.

8. Operating room lamp according to claim 5, wherein each angle sensor comprises a Hall generator.

* * * * *